US012797420B2

(12) United States Patent
Vitti

(10) Patent No.: US 12,797,420 B2
(45) Date of Patent: Nov. 17, 2026

(54) FORMULATION AND TREATMENT FOR OPHTHALMIC DISORDERS

(71) Applicant: AVAV LABS LLC, Lee's Summit, MO (US)

(72) Inventor: Philipp R. Vitti, Kansas City, MO (US)

(73) Assignee: AVAV LABS LLC, Lee's Summit, MO (US)

( * ) Notice: Subject to any disclaimer, the term of this patent is extended or adjusted under 35 U.S.C. 154(b) by 61 days.

(21) Appl. No.: 17/394,628

(22) Filed: Aug. 5, 2021

(65) Prior Publication Data

US 2022/0249575 A1 Aug. 11, 2022

Related U.S. Application Data

(60) Provisional application No. 63/132,551, filed on Dec. 31, 2020.

(51) Int. Cl.

| | |
|---|---|
| ***A61K 35/51*** | (2015.01) |
| ***A61K 35/14*** | (2015.01) |
| ***A61K 35/16*** | (2015.01) |
| ***A61K 35/28*** | (2015.01) |
| ***A61K 35/50*** | (2015.01) |
| ***A61K 38/18*** | (2006.01) |
| ***A61K 38/20*** | (2006.01) |
| ***A61P 27/06*** | (2006.01) |

(52) U.S. Cl.

CPC .............. *A61K 35/51* (2013.01); *A61K 35/14* (2013.01); *A61K 35/16* (2013.01); *A61K 35/28* (2013.01); *A61K 35/50* (2013.01); *A61K 38/18* (2013.01); *A61K 38/1808* (2013.01); *A61K 38/1825* (2013.01); *A61K 38/185* (2013.01); *A61K 38/1866* (2013.01); *A61K 38/1875* (2013.01); *A61K 38/2006* (2013.01); *A61K 38/2013* (2013.01); *A61K 38/202* (2013.01); *A61K 38/2026* (2013.01); *A61K 38/2033* (2013.01); *A61K 38/204* (2013.01); *A61K 38/2046* (2013.01); *A61K 38/2053* (2013.01); *A61K 38/206* (2013.01); *A61K 38/2066* (2013.01); *A61K 38/2073* (2013.01); *A61K 38/208* (2013.01); *A61K 38/2086* (2013.01); *A61P 27/06* (2018.01)

(58) Field of Classification Search

None

See application file for complete search history.

(56) References Cited

PUBLICATIONS

The Human Protein Atlas, BDNF (Tissue expression of BDNF—Summary—The Human Protein Atlas, accessed May 4, 2023).*

The Human Protein Atlas (Tissue expression of FGF7—Summary—The Human Protein Atlas, accessed May 4, 2023).*

The Human Protein Atlas (Tissue expression of GDF11—Summary—The Human Protein Atlas, accessed May 4, 2023).*

The Human Protein Atlas (<Tissue expression of BMP2—Summary—The Human Protein Atlas, accessed May 5, 2023).*

Siddesh et al. (Stem Cell Investig, 2021;8:3;2021).*

Ziganshina et al. (Aca Naturae, Jul.-Sep. 2016; 8(3):59-71).*

McPhee (Molecules. Nov. 19, 2014; 19(11): 19066-19077), (Year: 2014).*

* cited by examiner

*Primary Examiner* — Tara L Martinez

(74) *Attorney, Agent, or Firm* — Polsinelli PC

(57) ABSTRACT

The disclosure provides therapeutic ophthalmic formulations, kits, and uses thereof in the treatment of eye pathologies.

19 Claims, No Drawings

Specification includes a Sequence Listing.

FORMULATION AND TREATMENT FOR OPHTHALMIC DISORDERS

CROSS-REFERENCE TO RELATED APPLICATIONS

This application claims the benefit of U.S. Provisional Patent Application Ser. No. 63/132,551, filed Dec. 31, 2020, the entire contents of which are hereby incorporated herein by reference.

INCORPORATION BY REFERENCE OF A SEQUENCE LISTING

This application contains a Sequence Listing that has been submitted electronically in ASCII format via Patent Center and is hereby incorporated by reference in its entirety. The ASCII copy, created on Mar. 5, 2024, is named 116528-758454_ST25.txt and is 4,096 bytes in size.

FIELD OF THE INVENTION

The present invention is in the field of medicine. Moore particularly, the invention relates to formulations and treatment for ophthalmic disorders.

BACKGROUND OF THE INVENTION

There are many types of ophthalmic diseases and disorders which afflict the mammalian eye. These include viral and bacterial infections and wounds such as abrasions, interocular pressure problems and degeneration. Healing and recovery from these disorders can be complex and require lengthy periods of time. For example, wound healing may require different stages, including cell migration, cell proliferation, re-stratification, as well as matrix deposition and tissue remodeling.

To maintain vision, proper healing is vital and may need to be accomplished in a timely fashion Thus, these disorders have been treated with various methods, with limited therapeutic effect.

Transplantation of certain eye tissues and regenerative medicine have been used to treat certain eye disorders. For example, to treat disorders of the cornea, cadaver corneal transplantation (keratoplasty) and limbal transplantation have been done, as well as transplantation of mucosal epithelial stem cells and adipose stem to the site of injury.

However, such treatment requires long-term immunosuppression that involves high risks of serious eye and systemic complications, including infection, glaucoma, and liver dysfunction.

To solve these problems, ocular surface reconstruction using cultured limbal or oral mucosal epithelial stem cells has been successfully used to treat various eye disorders.

However, cell sheets must be fabricated in a cell processing center (CPC) under good manufacturing practice conditions for clinical use, and the expenses of maintaining a CPC are too high for all hospitals to cover.

Eye patching has been used to reduce pain caused by certain eye disorders by reducing blinking and decreasing eyelid-induced trauma to the damaged cornea. However, patching may retard the healing process, due to decreased oxygen delivery, increased moisture, and a higher chance of infection.

Topical nonsteroidal anti-inflammatory drugs (NS AIDs) such as diclofenac (Voltaren) and ketorolac (Acular) are modestly useful in reducing pain from corneal abrasions.[2] However, topical anesthetics can retard healing and cause corneal damage.

Antibiotics in the form of drops and ointments have been used to treat various corneal disorders (e.g., baci-tracin [AK-Tracin], erythromycin, gentam Ycin [Garamycin] ciprofloxacin [Ciloxan], gentamycin, ofloxacin [Ocuflox]).

Thus, what is still needed are better therapeutics that can treat ophthalmic disorders quickly and effectively such that vision is not lost.

SUMMARY

It has been discovered that a combination of certain umbilical cord/placental tissue and certain growth factors, is effective in treating many common eye disorders. This discovery has been exploited to develop the present disclosure, which, in part, is directed to therapeutic ophthalmic formulations, kits, and methods of treating certain ophthalmic disorder.

In one aspect, the present disclosure is directed to an ophthalmic formulation comprising an umbilical cord/placental tissue selected from the group consisting essentially of blood, plasma, a plurality of mesenchymal nucleated cells (MNCs), a plurality of mesenchymal signaling cells (MSCs), and combinations thereof Brain-Derived Neurotrophic Factor (BDNG); Fibroblast Growth Factor-7); Growth Differentiation Factor 11 (GDF-11); and Interleukin-10 (IL-10). In some embodiments, the umbilical cord/placental tissue in the formulation is blood, plasma, a plurality of MNCs, or a plurality of MSCs. In other embodiments, the umbilical cord/placental tissue in the formulation is blood and plasma, or is plasma and a plurality of MNCs, or is a plurality of MNCs and a plurality of MSCs, or is blood and a plurality of MNCs, or is blood and a plurality of MSCs, or is plasma and a plurality of MSCs. In some embodiments, the umbilical cord/placental tissue in the formulation is blood, plasma, and a plurality of MSCs, or is blood, plasma, and a plurality of MNCs, or is plasma, a plurality of MNCs, and a plurality of MNCs. In a particular embodiment, the umbilical cord/placental tissue in the formulation is blood, plasma, a plurality of MNCs, and a plurality of MNCs.

In some embodiments, the formulation further comprises BCL-157 and or hyaluronic acid. In certain embodiment, the formulation further comprising a growth factor selected from the group consisting of FGF-4, HGF, SCF, ICAM-1, TIMP-1, TIMP-2, TGF-Beta 3, TNFR1, EGF, EGF-R, VEGF, VEGF R3, VEGF R2, PDGF-BB, PDGF-AA, MIP-1, IL-1RA, IL-1, GDNF, GDF15, SCF, IGFBP1, IGFBP2, IGFBP3, IGFBP4, IGFBP5, IGFBP6, IL-1 through IL-37, Eotaxin, Eotaxin 2, IFN-gamma, MIP-1a, MIP-1b, TNFb, TNFa, TNF R, PIGF, BMP-2, BMP-9, BMP-4, BMP-5, BMP-7, and combinations thereof.

In another aspect, the disclosure provides a method of treating an eye pathology in a subject suffering therefrom, comprising administering to the subject an amount of the formulation described above and herein, the amount being effective to reduce a symptom of the eye pathology. In some embodiments, the eye pathology is glaucoma, oxidative stress, macular degeneration, retinal degeneration, corneal abrasion, inflammation, cataracts, or dry eye.

In yet another aspect, the disclosure provides a kit comprising dosage units of the ophthalmic formulation as described above and herein.

Also provided by the disclosure are use of the ophthalmic formulation described above and herein in the treatment of an eye pathology, and preparation of a formulation for use in treating ophthalmic disorders as described herein.

DETAILED DESCRIPTION

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the viral pathology being treated.

As used herein, the term "prevent" or "prevention" means no infection, disorder, or pathological development if none had occurred, or no further disorder or pathological development if there had already been development of the disorder or infection. Also considered is the ability of one to prevent some or all of the symptoms associated with the disorder or disease.

As used herein, the term "patient," "individual," or "subject" refers to a human or a non-human mammal. Non-human mammals include, but are not limited to, livestock and pets, such as ovine, bovine, porcine, canine, feline and marine mammals.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the terms "eye pathology, and "ophthalmic pathology" refer to the repercussions of an eye disorder, disease, or injury.

As used herein, the term "pharmaceutically acceptable" refers to a material, such as a carrier or diluent, which does not abrogate the biological activity or properties of the ketone or other therapeutic agent, and is relatively non-toxic, i.e., the material may be administered to an individual without causing undesirable biological effects or interacting in a deleterious manner with any of the components of the composition in which it is contained.

The term "pharmaceutical composition", or "formulation" refers to at least one ketone and/or salt thereof, according to the disclosure in a pharmaceutically acceptable carrier, and may encompasses another or other therapeutic agents.

An "oral dosage form" includes a unit dosage form prescribed or intended for topical or interocular administration.

Pharmaceutical Formulation

This disclosure provides a therapeutic formulation that treats various ophthalmic pathologies which may result from an eye disease, disorder, or injury. It also provides a physical barrier in the eye against external environment and thus provides prophylactic protection. It acts as an anti-scarring, anti-inflammatory, anti-microbial, and anti-angiogenic agent, and is useful for supporting ocular surface health reconstruction.

The formulation comprises at least one of the following components: umbilical cord/placental blood, umbilical cord/placental plasma, umbilical cord/placental mesenchymal signaling cells, and/or umbilical cord/placental mono-nucleated cells. The formulation also comprises the following growth factors: Brain-Derived Neurotrophic Factor (BDNG), Fibroblast Growth Factor-7 (FGF-7), Growth Differentiation Factor 11 (GDF-11), and Interleukin-10 (IL-10). This formulation may also comprise of hyaluronan (hyaluronic acid).

The formulation may also comprise the BPC-157 peptide in combination with the at least one of umbilical cord/placental blood, plasma, mesenchymal signaling cells, and/or mono-nucleated cells. This formulation may also comprise hyaluronan.

Each of the possible components of the formulation are described in detail below.

A. Umbilical Cord/Placental Blood

The blood component can be obtained from a human umbilical cord, or blood of the placenta. Blood is obtained from umbilical cord or placental tissues by methods known to those with skill in the art.

B. Plasma

Plasma is the liquid portion of whole mammalian blood that does not contain red blood, white blood cells, or platelets. It makes up 55% of whole blood, and contains water, salts, enzymes, antibodies and other dissolved proteins, including serum albumins, globulins, fibrinogen, hormones, glucose, cloning factors, and electrolytes.

Plasma can be obtained from blood from a human umbilical cord, placenta, or any tissue therefrom by centrifugation to remove blood cells. Plasma can be obtained from blood obtained from placenta or umbilical cord. Alternatively, plasma may be obtained by methods known to those with skill in the art form the circulatory system of human donors, such as, but not limited to, those under the age of about 30 years of age.

C. Medicinal Signaling Cells (MSCs)

MSCs, also known as mesenchymal stem cells and mesenchymal stromal cells, are multipotent cells that can differentiate into a variety of cell types, and are self-renewing. MSCs facilitate wound repair by modulating cellular responses in the cells of surrounding tissue and immune cells, creating a pro-regenerative and anti-inflammatory environment. MSCs possess minimal susceptibility to malignant transformation and can avoid immune cell recognition.

These cells are obtainable from blood sources of including placenta, bone marrow aspirate, hemopoietic stem cells of the blood, or can be obtained from certain tissues, including placenta, umbilical cord or Wharton's jelly, dermal, or adipose tissue. They can be isolated from blood by centrifugation and/or density gradient layering isolation techniques to remove the plasma and the blood. These cells are expanded from about 10 million cells/ml cord blood to about 350 million/ml by incubation in a growth medium such as, but not limited to, Rooster Nourish MSC Growth Medium (Rooster Bio), and using e.g., such as, but not limited to, plastic adhesion techniques via 2D or 3D scaling. For example, they can be present in the formulation at about $2.5\times10^5$-$6.0\times10^6$/ml.

D. Mono-Nucleated Cells (MNCs)

MNCs, also known as mono nucleated cells, also referred to as total nucleated cells are obtained from the placenta, blood, or tissue. These blood cells have a single, round nucleus, and are lymphocytes and monocytes. They can be obtained from circulating blood, and when isolated from circulating blood, they are called peripheral blood mononuclear cells (PBMC). These cells may also be obtained from tissue such as m but not limited to, the umbilical cord, spleen, and bone marrow. They can be obtained by any method known to those with skill in the art, such as by centrifugation and/or density gradient layering isolation techniques to remove the plasma and the blood.

These cells are expanded from about 10 million cells/ml cord blood to about 350 million/ml in a growth medium as described above. For example, they can be present in the formulation at about $2.5\times10^5$-$1.0\times10^7$/ml.

E. Growth Factors

Formulations according to the disclosure comprise certain growth factors. These include brain derived neurotrophic factor (BDNF), fibroblast growth factor 7 (FGF-7), interleukin 10 (IL-10), and growth differentiation factor 11 ((GDF-11) which are each present in the formulation at about 10 μg/ml to about 1,000 μg/m.

BDNF is a member of the neurotrophin family of growth factors. It slows down retinal degeneration, in particular, degeneration and apoptosis of retinal epithelial cells and photoreceptors. It is commercially obtainable from e.g., Creative BioMart.

FGF-7 promotes corneal wound healing, protects human corneal epithelial cells from hypoxia-induced disruption of barrier function, promotes limbal stem cell proliferation, and modulates corneal epithelium renewal and homeostasis. It is released locally upon injury or tissue remodeling. It is commercially obtainable, e.g., from Stem Cell Technologies.

I1-10, also known as human cytokine synthesis inhibitory factor (CSIF), is an anti-inflammatory cytokine possessing pleiotropic effects in immunoregulation and inflammation and protects against MHC class II antigens. It has anti-inflammatory and chemotactic action on macrophages which contribute to the removal of intraretinal cell debris and to the function normally carried out by RPE. It is commercially obtainable Stem Cell Technologies.

GDF-11, also known as bone morphogenetic protein 11 (BMP-11), is a protein that is a member of the Transforming growth factor beta family. It is expressed in many tissues, including the nervous system and the retina. It acts as a cytokine and controls the competence of progenitor cells to regulate numbers of retinal ganglionic cells developing in the retina. It is commercially obtainable, e.g., from Stem Cell Technologies.

The formulation can further comprises other growth factors such as at least one of FGF-4, HGF, SCF, ICAM-1, TIMP-1, TIMP-2, TGF-Beta 3, TNFR1, EGF, EGF-R, VEGF, VEGF R3, VEGF R2, PDGF-BB, PDGF-AA, MIP-1, IL-1RA, IL-1, GDNF, GDF15, SCF, IGFBP1, IGFBP2, IGFBP3, IGFBP4, IGFBP5, IGFBP6, IL-1 through IL-37, Eotaxin, Eotaxin 2, IFN-gamma, MIP-1a, MIP-1b, TNFb, TNFa, TNF R, PIGF, BMP-2, BMP-9, BMP-4, BMP-5, and/or BMP-7. These growth factors are also commercially available from multiple sources.

F. BPC-157

BPC-157, also known as PL 14736, is a pentadecapeptide, having an ammo acid sequence Gly-Glu-Pro-Pro-Pro-Gly-Lys-Pro-Ala-Asp-Asp-Ala-Gly-Leu-Val (SEQ ID NO: 1). It was originally derived from a gastric juice protein BPC, and can be synthesized or commercially obtained e.g., from Integrative Peptides, Hudson, MI. It is present in certain formulations according to the disclosure at about 1 mg/ml to about 10 mcg/ml.

G. Hyaluronic Acid

Hyaluronic acid (HA), also called hyaluronan, is an anionic, non-sulfated glycosaminoglycan having the chemical formula $(C_{14}H_{21}NO_{11})_n$. It is a linear, unbranched, alternating polymer composed of two monosaccharides: β(1,4)-N-acetyl-D-glucosamine and β(1,3)-D-glucuronic acid. HA is the major constituent of the extracellular matrix or scaffold secreted by cells throughout connective, epithelial, and neural tissues. In addition to being a structural component of tissues, it is a signaling molecule, regulating cell adhesion and motility and mediating cell proliferation and differentiation. It is present in certain formulations according to the disclosure at about 0.01 ng/ml to about 3.5 mg/ml. It is commercially obtainable, e.g., from Millipore-Sigma, St. Louis, MO.

The formulations according to the disclosure can also comprise a pharmaceutically acceptable carrier which does not interfere with the therapeutic activity of any of the components described above.

The term "pharmaceutically acceptable carrier" is to be understood herein as referring to any substance that may, medically, be acceptably administered to a subject, together with the components of the formulation, according to the disclosure, and which does not undesirably affect the pharmacological and synergistic activity of the components. A "pharmaceutically acceptable carrier" may be, for example, a pharmaceutically acceptable member(s) comprising of diluents, preservatives, solubilizers, emulsifiers, adjuvant, tonicity modifying agents, buffers as well as any other physiologically acceptable vehicle. These formulations are prepared with the pharmaceutically acceptable carrier in accordance with known techniques, for example, those described in Remington, The Science and Practice of Pharmacy (9th Ed. 1995).

The components of an exemplary formulation according to the disclosure are

| COMPONENT | AMOUNT |
|---|---|
| MNCs | $2.5\times10^5$-$1.0\times10^7$/mL |
| MSCs | $2.5\times10^5$-$6.0\times10^6$/mL |
| Plasma/Blood | 10%-50% vol/vol |
| IL-10 | 10 pg/ml-100 μg/ml |
| BDNF | 10 pg/ml-100 μg/ml |
| GDF-11 | 10 pg/ml-100 μg/ml |
| FGF-7 | 10 pg/ml-100 μg/ml |
| BPC-157 | 1 μg/ml-50 μg/ml |

-continued

| COMPONENT | AMOUNT |
|---|---|
| PBS/water | 10%-50% vol/vol |
| Hyaluronic acid | 0.01 ng/mL-3.5 mg/mL |

The pharmaceutical formulations are prepared for topical or intraocular use in liquid form. These formulations may be in unit dosage forms such as drops, sterile parenteral solutions or suspensions, metered aerosol or liquid (nebulized) sprays, or ampoules.

The formulations may be homogeneous, i.e., the components are dispersed evenly throughout the liquid composition so that the composition may be readily subdivided into equally effective unit dosage.

Injectable or topical dosage forms may be sterilized in a pharmaceutically acceptable fashion, for example by steam sterilization of an aqueous solution sealed in a vial under an inert gas atmosphere at 120° C. for about 15 minutes to about 20 minutes, or by sterile filtration of a solution through an about 0.2 μM or smaller pore-size filter, optionally followed by a lyophilization step, or by irradiation of a composition containing an inhibitor of the present disclosure by means of emissions from a radionuclide source.

Once the components are combined, the formulation may be stored via cryopreservation or lyophilization.

For cryopreservation, the liquid formulation is separated into dosage units in vials which are placed into a Slow Rate freezer, e.g., from Planer, and frozen at −1° C. to −5° C./2 minutes to 10 minutes temperature drop rate until they reach −80° C. The vials are then placed into cryogenic storage for up to 2 years. When delivered to a provider, the vials may be stored in a residential freezer before use for up to—a year. The formulation is thawed and brought to room temperature prior to application.

For lyophilization, the liquid formulation is placed into a sterile freeze guard tray that can handle −80° C. The formulation is covered with a commercially available permeable membrane tray, e.g., from GORE, that allows for water vapor to be released from the liquid. The formulation is frozen at between −25° C. to −35° C. and subjected to compression until the moisture content of the powdered formulation is less than 12%. The lyophilized formulation can be kept at room temperature post-lyophilization. Before use it is reconstituted in saline at the concentration determined by one with skill in the art.

A therapeutically effective dosage of the formulation according to the disclosure depends on the ophthalmic pathology being treated, and may vary from subject to subject. Factors affecting dosage include age, the subject's genetics, the diagnosed condition of the subject, and its severity. A therapeutically effective dose and frequency of administration of a dosage form may be determined in accordance with routine pharmacological procedures known to those skilled in the art. For example, dosage amounts and frequency of administration may vary or change as a function of time and severity of the disorder. A dosage from about 1 dose to about 6 doses per day or from about 1 to about 3 doses per day are useful.

The formulations may take the form of eye drops that are topically provided to the cornea of the eye, and can be provided in dosage units of about 0.1 ml to about 1.0 ml. The drops can be applied according to the disorder being treated, and the severity of the disorder, as instructed by one with skill in ophthalmology.

Alternatively, when treating a subject for a particular ophthalmic disorder with the formulation according to the disclosure, treatment may also include administration of another therapeutic formulation different than the formulation.

Eye Disorders and Diseases Treatable with the Formulation

The formulation according to the disclosure can be used to treat dry eye disease (DED). DED affects the tears and ocular surface, and results in symptoms of discomfort, visual disturbance, and tear film instability with potential damage to the ocular surface. It can be accompanied by increased osmolarity of the tear film and inflammation of the ocular surface which can lead to the onset of more detrimental diseases of the eye. DED is caused by a lack of adequate tears, which may be the result of certain diseases, such as rheumatoid arthritis, Sjögren's syndrome, thyroid disease, and lupus, blepharitis (when eyelids are swollen or red), entropion (when eyelids turn in); ectropion (eyelids turn outward), smoke, wind or a very dry climate, extended computer screen viewing, reading and other activities that reduce blinking, the use of contact lenses, refractive eye surgery, such as LASIK, and certain medication such as diuretics, beta-blockers, antihistamines, sleeping pills, Anxiety and antidepressant medicines, and heartburn medicines.

The formulation may also be used to mitigate oxidative stress in the eye. Oxidation stress is involved in the development and progression of certain neurodegenerative eye disorders. In addition, aging, gene abnormalities, and excess exposure to exogenous oxidative stressors (e.g., smoke and light exposure) increase oxidative stress in the eye. Oxidative stress is caused by an imbalance between the antioxidant defense system and the production of reactive oxygen species (ROS). Excess ROS leads to oxidative damage to DNA, proteins, lipids, and mitochondria.

Inflammation of the eye is also treatable with the formulation according to the invention. Inflammation may result from constant dry eyes, trauma and environmental irritation, and infection by viruses or bacteria. Inflammation affects retinal pigment epithelial cells and endothelial cells. It causes shifts in the endothelial cell phenotype, increasing the expression of inflammatory mediators, unhealthy proangiogenic amounts of growth factors, and proinflammatory cytokines, and iNOS activation. Proinflammatory cytokines such as tumor necrosis factor-(TNF-)α, are induced in macrophages and healthy RPE cells by the medium of dying cells exposed to oxidative stress. Conversely, proinflammatory cytokines, such as TNF-α, interleukin-1β (IL1β), or interferon-γ (IFN-γ), induce intracellular and extracellular ROS production in human RPE cells. These proinflammatory cytokines are upregulated in the eyes of patients with glaucoma, age-related macular degeneration, diabetic retinopathy, or retinal vein occlusion. In addition, RPE interacts with endothelial cells directly and puts the proangiogenic growth factors and pro inflammatory cytokines into cytokine storm which leads to retinal diseases such as macular degeneration.

Cataracts can be treated with the formulation according to the disclosure. Cataracts, including subcapsular, nuclear, and cortical cataract, is the clouding of the eye's natural lens. It is the most common cause of vision loss in people over age 40 and is also the principal cause of blindness in the world. It can be caused by aging, family genetics, diabetes, eye injury, eye surgery, radiation, ultraviolet radiation, hypertension, obesity, smoking, medications such as corticosteroids.

Retinal degenerative diseases can be treated with the formulation according to the invention. These diseases are a group of heterogeneous conditions which include Age-related Macular Degeneration (AMD), retinitis pigmentosa, and diabetic retinopathy. Numerous factors, such as oxidative stress, genetic diseases, light-induced damage, chemical insults, vascular defects or aging, contribute to the development of retinal degeneration.

The formulation can also be used to treat progressive degeneration of the retinal neurons. Such degeneration results in a group of heterogeneous conditions which include Age-related Macular Degeneration (AMD), retinitis pigmentosa, and diabetic retinopathy. As the human retina has limited self-regenerative nature, visual impairment due to retinal degeneration is difficult to treat. Numerous factors, such as oxidative stress, genetic diseases, light-induced damage, chemical insults, vascular defects or aging, contribute to the development of retinal degeneration.

Age-related macular degeneration (AMD), both wet and dry, can be treated with the formulation according to the disclosure. AMD is the leading cause of blindness in elderly individuals throughout the world, and approximately 196 million people suffer from AMD.

There are several events that occur during the development of AMD, such as oxidative stress, choroidal neovascularization, the formation of drusen and RPE dysfunction, apoptosis, activating immune system, senescent loss of homeostatic control, and Bruch's membrane abnormalities. The vessels within Bruch's membrane or the sub-RPE space develop very weak; therefore, hemorrhage and have vascular leakage causing damage to the retina leading to further vision loss.

With aging, antioxidant level declines and ROS level increases, ensuring oxidative stress. By aging, macular carotenoids level, glutathione S-transferase-1 expression level, and vitamin E level are decreased. In contrast lipofuscin, mitochondrial DNA damage in retina, advanced lipid peroxidation, and glycation end products are increased. Aging and environmental damages change the homeostasis of these factors, which means that the rate of AMD development is high in elderly individuals.

The formulation can be used to treat glaucoma. Glaucoma affects more than 70 million people worldwide with approximately 10% being bilaterally blind, making it the leading cause of irreversible blindness for people over 60 in the world. Glaucoma includes a group of ocular multifactorial pathologies comprising one or all of the intraocular pressure (IOP) increase, degenerative phenomena affecting the optic nerve head, and a progressive deterioration of the visual field. It is a central nervous system, age-related neurodegenerative disease that causes neurotoxic waste build up and anatomy blockages, resulting in oxidative stress, glial activation, neurotrophin deprivation, and mitochondrial dysfunction.

Corneal epithelia defects are also treatable with the formulation according to the disclosure. The cornea is the transparent, outermost layer of the eye that refracts light that enters the eye onto the lens and is essential for vision. The multi-layered corneal epithelium acts as a protective barrier to infectious and maintains its smooth optical surface by regenerating cells in the basal cell layer. Disruptions in this protective layer can render the eye susceptible to infection, stromal ulceration, perforation, scarring, and decreased visual acuity. Corneal epithelial defects are focal areas of epithelial (outermost corneal layer) loss; they can be due to mechanical trauma, corneal dryness, chemical burns, infectious and immunological disorders, basement membrane disorders, neurotrophic diseases, post-surgical changes, infection, or any other of a variety of etiologies. Persistent corneal epithelial defects (PED) are one of the challenging and common problems in ophthalmology practice.

Other disorders that can be treated with the formulation according to the disclosure include corneal disorders, eye-strain, red eyes, retinal, corneal, and epithelial tares, defects, and degeneration, chemical and other burns, and injuries.

Treatment

A vial of cryopreserved formulation is removed from the freezer and thawed for up to 5 minutes at room temperature, or the lyophilized formulation is removed from dry dark storage and reconstituted in 0.25 mL of sterile water or 0.9% saline before use.

The content of one vial is applied to the affected eye, or the contents of two vials is used to apply to both eyes in equal amount using a dropper or other type of applicator if topically applied, or using a syringe if applicated intraocularly. Application can be from once a day to about 6 times a day. The vial of formulation can be kept for 30-60 days at −20° C. or until expiration date (e.g., up to a year) in −80° C. freezer.

Reference will now be made to specific examples illustrating the disclosure. It is to be understood that the examples are provided to illustrate exemplary embodiments and that no limitation to the scope of the disclosure is intended thereby.

Example 1

Phase 1 Study for Treatment of Glaucoma

Ten (10) subjects 45-75 years of age diagnosed to be suffering from glaucoma for at least six (6) months, but having intraocular pressure that stable for at least for three (3) months and having a visual acuity of each eye (measured by using visual acuity charts projector) of not less than 0.1, undergo a 90-day regimen of treatment as follows.

Subjects are screened for the parameters described above, provide a history, and undergo a physical examination and baseline testing prior to treatment. These tests include filling out a Health Assessment Questionnaire (HAQ), and undergoing tonometry to determine inner eye pressure, ophthalmoscopy, and perimetry (visual field testing).

0.25 ml formulation is dropped into each eye. This is repeated 3 times a day for 30 days. Thirty (30) minutes post-application, vital signs are measured and tonometry, ophthalmoscopy, and perimetry are performed.

Within about 24 hours to about 48 hours of a treatment, subjects are followed up for signs of adverse reactions. These include changes in the structure of the fundus of the eye assessed by optical coherence tomography and changes of optic disc, neuroretinal rim and macula, retinal nerve fiber layer thickness, changes in visual field from baseline as assessed by computer perimetry; and changes in intraocular pressure. Subjects are encouraged to share ongoing reports of progress or issues related to treatment. Data collection is uploaded to Pathway Research Institute website user platform for review and auditing as needed and to track secondary outcome measures.

Four (4) weeks from the first application, the same pre-administration testing is performed, followed by a second application of formulation and second post-administration testing. This procedure is repeated once a month for three (3) months. Twenty-four (24) weeks from the first application, HAQ, tomometry, ophthalmoscopy, perimetry and blood count/comprehensive metabolic panel are performed.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A sterilized liquid therapeutic formulation comprising:

plasma;

a plurality of isolated mesenchymal nucleated cells (MNCs);

a plurality of isolated mesenchymal signaling cells (MSCs);

Brain-Derived Neurotrophic Factor (BDNF);

Fibroblast Growth Factor-7 (FGF-7);

Growth Differentiation Factor 11 (GDF-11);

Interleukin-10 (IL-10);

BPC-157; and 10-50% vol/vol of a pharmaceutically acceptable carrier;

wherein the plurality of isolated MNCs and/or the plurality of isolated MSCs have been isolated and expanded in culture from an umbilical cord and/or placental tissue.

2. The therapeutic formulation of claim 1, further comprising hyaluronic acid.

3. The therapeutic formulation of claim 1, further comprising a growth factor selected from the group consisting of FGF-4, HGF, SCF, ICAM-1, TIMP-1, TIMP-2, TGF-Beta 3, TNFR1, EGF, EGF-R, VEGF, VEGF R3, VEGF R2, PDGF-BB, PDGF-AA, MIP-1, IL-1RA, IL-1, GDNF, GDF15, SCF, IGFBP1, IGFBP2, IGFBP3, IGFBP4, IGFBP5, IGFBP6, IL-1 through IL-37, Eotaxin, Eotaxin 2, IFN-gamma, MIP-Ia, MIP-Ib, TNFb, TNFa, TNF R, PIGF, BMP-2, BMP-9, BMP-4, BMP-5, BMP-7, and combinations thereof.

4. A kit comprising dosage units of the therapeutic formulation of claim 1.

5. The therapeutic formulation of claim 1, comprising $2.5\times10^5$ cells/mL to $1.0\times10^7$ cells/mL of mesenchymal nucleated cells (MNCs).

6. The therapeutic formulation of claim 1, comprising $2.5\times10^5$/mL to $6.0\times10^6$/mL of mesenchymal signaling cells (MSCs).

7. The therapeutic formulation of claim 1, comprising $2.5\times10^5$ cells/mL to $1.0\times10^7$ cells/mL of mesenchymal nucleated cells (MNCs) and $2.5\times10^5$/mL to $6.0\times10^6$/mL of mesenchymal signaling cells (MSCs).

8. The therapeutic formulation of claim 1, comprising 10-50% vol/vol of plasma.

9. The therapeutic formulation of claim 1, comprising 10 pg/mL-100 μg/mL of IL-10.

10. The therapeutic formulation of claim 1, comprising 10 pg/mL-100 μg/mL of GDF-11.

11. The therapeutic formulation of claim 1, comprising 10 pg/mL-100 μg/mL of FGF-7.

12. The therapeutic formulation of claim 1, comprising 10 pg/mL-100 μg/mL of BDNF.

13. The therapeutic formulation of claim 1, comprising 1 μg/mL-50 μg/mL of BPC-157.

14. The therapeutic formulation of claim 2, comprising 0.01 ng/ml-3.5 mg/ml of hyaluronic acid.

15. The therapeutic formulation of claim 1, wherein the formulation is prepared for topical or intraocular use.

16. The therapeutic formulation of claim 15, wherein the formulation is prepared as eye drops.

17. The sterilized liquid therapeutic formulation of claim 1, wherein the pharmaceutically acceptable carrier is water and/or phosphate buffered saline (PBS).

18. A sterilized liquid dosage form for topical or intraocular administration comprising:

10-50% vol/vol plasma;

$2.5\times10^5$ cells/mL to $1.0\times10^7$ cells/mL of isolated mesenchymal nucleated cells (MNCs);

$2.5\times10^5$/mL to $6.0\times10^6$/mL of isolated mesenchymal signaling cells (MSCs);

10 pg/mL-100 μg/mL of BDNF Brain-Derived Neurotrophic Factor (BDNF);

10 pg/mL-100 μg/mL of Fibroblast Growth Factor-7 (FGF-7);

10 pg/mL-100 μg/mL of Growth Differentiation Factor 11 (GDF-11);

10 pg/mL-100 μg/mL of Interleukin-10 (IL-10);

1 μg/mL-50 μg/mL of BPC-157;

0.01 ng/ml-3.5 mg/mL of hyaluronic acid; and 10-50% vol/vol of a pharmaceutically acceptable carrier.

19. A lyophilized therapeutic formulation comprising:

plasma;

a plurality of isolated mesenchymal nucleated cells (MNCs);

a plurality of isolated mesenchymal signaling cells (MSCs);

Brain-Derived Neurotrophic Factor (BDNF);

Fibroblast Growth Factor-7 (FGF-7);

Growth Differentiation Factor 11 (GDF-11);

Interleukin-10 (IL-10); and

BPC-157;

wherein the plurality of isolated MNCs and/or the plurality of isolated MSCs have been isolated and expanded in culture from an umbilical cord and/or placental tissue.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial sequence
<220> FEATURE:
<223> OTHER INFORMATION: Synthetic Construct

<400> SEQUENCE: 1

Gly Glu Pro Pro Pro Gly Lys Pro Ala Asp Asp Ala Gly Leu Val
1               5                   10                  15
```